United States Patent
Sakurai et al.

(10) Patent No.: US 6,811,789 B2
(45) Date of Patent: Nov. 2, 2004

(54) FRAGRANT COMPOSITION HAVING MOSQUITO-REPELLING EFFECT

(75) Inventors: Kazutoshi Sakurai, Hiratsuka (JP); Masataka Miyasaka, Hiratsuka (JP); Yasutaka Mishima, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/282,156

(22) Filed: Oct. 29, 2002

(65) Prior Publication Data

US 2003/0138470 A1 Jul. 24, 2003

(30) Foreign Application Priority Data

Nov. 1, 2001 (JP) ..................................... P. 2001-336249

(51) Int. Cl.⁷ .............................................. A01N 25/02
(52) U.S. Cl. ....................... 424/405; 424/401; 424/736; 424/750; 424/DIG. 10; 574/675; 574/693; 574/703; 574/729; 574/739; 574/919
(58) Field of Search ................................ 424/405, 406, 424/407, 419, 420, 47, 59, 60, 401, 76.8, 78.02, DIG. 10, 750, 736; 514/675, 693, 703, 729, 739

(56) References Cited

U.S. PATENT DOCUMENTS 5,621,013 A 4/1997 Beldock et al.
6,287,550 B1 * 9/2001 Trinh et al. ................. 424/76.6
2002/0032147 A1 * 3/2002 Poley et al. .................. 512/25

OTHER PUBLICATIONS

Thorsell et al. HCA Plus 1998:624126 Phytomedicine 5(4) 311–323 Efficacy of Plant extracts.*

* cited by examiner

Primary Examiner—Neil S. Levy
(74) Attorney, Agent, or Firm—Sughrue Mion, PLLC

(57) ABSTRACT

A mosquito-repelling agent which is gentle to human and environment and safe, and has an excellent mosquito-repelling effect almost equal to the effect of DEET and also an excellent persistency of the effect. The mosquito-repelling agent comprises a mixture of isomenthone, linalool, geraniol, citral and citronellol as an effective ingredient for a mosquito-repelling effect, which may be contained in a fragrant composition.

8 Claims, 1 Drawing Sheet

FRAGRANT COMPOSITION HAVING MOSQUITO-REPELLING EFFECT

FIELD OF THE INVENTION

The present invention relates to a fragrant composition having a mosquito-repelling effect, which comprises containing a mixture made of specific compounds obtainable from plant essential oils as an effective ingredient.

That is, it relates to a fragrant composition having a mosquito-repelling effect, which comprises containing a mixture made of isomenthone, linalool, geraniol, citral and citronellol as an effective ingredient.

Furthermore, it relates to a fragrant composition having a mosquito-repelling effect, wherein the mixture further contains a fatty acid having 8 to 10 carbon atoms.

BACKGROUND OF THE INVENTION

Heretofore, many mammals including human have continued to suffer from action of mosquitoes. For example, sucking of blood by a mosquito results in an itching sensation and an outbreak of a rush, dermatitis, or the like and hence causes a very unpleasant feeling. As one means for solving the problems of the suffering or unpleasant feeling, there is known a method of applying a mosquito-repelling agent to the surface of human skin.

N,N-Diethyl-m-toluamide (hereinafter, referred to as DEET) having a mosquito-repelling effect is currently employed commonly in various products as a mosquito-repelling agent. However, DEET has a remarkably high persistency of the mosquito-repelling effect, but it has problems of outbreak of dermatitis and cranial nerve injury when the use is continued for a long period of time, a possibility of carcinogenesis owing to its high skin-permeability, and a poor biodegradability and a high accumulative property.

Accordingly, a safe mosquito-repelling agent exerting no adverse effect on human and environment has been desired.

Thus, for the purpose of developing a mosquito-repelling agent which is gentle to the environment and safe to human body, and has a mosquito-repelling effect, the present inventors have focused on *Pelargonium citrosum* which is known to have a mosquito-repelling effect and isolated an essential oil from the plant.

However, it has been found that the essential oil of *Pelargonium citrosum* has a satisfactory mosquito-repelling effect but the sustained effect is not sufficient.

SUMMARY OF THE INVENTION

Therefore, it is an object of the invention to provide a mosquito-repelling agent which has an excellent mosquito-repelling effect almost equal to the effect of DEET, is gentle to the environment and safe to human body, and also has an excellent persistency. Furthermore, it is also an object to provide a mosquito-repelling fragrant composition having a pleasant smell for consumers.

As a result of intensive studies for solving the above problems, based on the information on fragrant ingredients obtained by the fragrance analysis and dynamic head space analysis of the distillate from steam distillation of *Pelargonium citrosum*, the inventors have found that a fragrant composition containing a mixture made of specific compounds, more specifically, a fragrant composition containing a mixture of the compounds having a specific weight ratio has a strong mosquito-repelling effect equal to or higher than the effect of DEET and also has a satisfactory persistency of the mosquito-repelling effect which is different from the distillate from steam distillation of *Pelargonium citrosum*.

In addition, the fragrant composition of the invention exhibits no irritation toward skin and has a high safety. Furthermore, the inventors have found the advantages that the fragrance tone can be widely changed by using other fragrant material(s) in combination and that the composition has less sticky feeling toward skin as compared with DEET. Based on the findings, they have accomplished the invention.

Namely, the invention relates to:

1) a fragrant composition having a mosquito-repelling effect, which comprises containing a mixture made of isomenthone, linalool, geraniol, citral and citronellol, as an effective ingredient;
2) the fragrant composition, wherein the weight ratio of the above compounds in the mixture is, on the basis of isomenthone, that linalool, geraniol, citral and citronellol are 0.5 to 2.0, 2.0 to 5.0, 0.5 to 2.0, and 2.0 to 4.0, respectively;
3) the fragrant composition, wherein the mixture further comprises a fatty acid having 8 to 10 carbon atoms;
4) the fragrant composition, wherein the weight ratio of the above fatty acid is 0.05 to 2.0 on the basis of isomenthone; and
5) the fragrant composition, wherein the fatty acid is decanoic acid and/or rhodinic acid.

Figure 1:
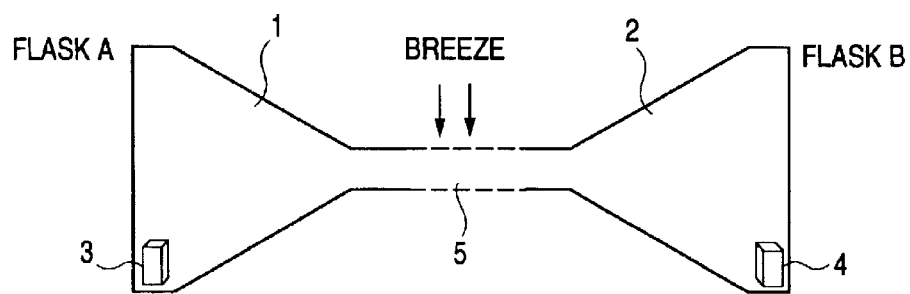
FIG. 1 is a cross-sectional view of an apparatus for measuring a mosquito-repelling effect for use in the invention.

In the figures, reference numerals respectively show the following meanings.

1: Flask A
2: Flask B
3: Sugar water
4: Sugar water
5: Wire netting
6: Flask C
7: Flask D
8: Air freshener
9: Sugar water
10: Sugar water
11: Wire netting

DETAILED DESCRIPTION OF THE INVENTION

The following will explain the invention in detail.

The fragrant composition having a mosquito-repelling effect contains a mixture made of isomenthone, linalool, geraniol, citral and citronellol, as an effective ingredient. As the compounds composing the above mixture, natural products obtainable from essential oils and the like or synthetic products may be employed. Also, commercially available products may be employed.

With regard to isomenthone, linalool, and citronellol, any compound of optically active compounds, mixtures thereof, and racemic compounds may be employed.

The weight ratio of the compounds composing the mixture is, on the basis of isomenthone (assuming as 1), preferably that linalool, geraniol, citral and citronellol are 0.5 to 2.0, 2.0 to 5.0, 0.5 to 2.0, and 2.0 to 4.0, respectively. More preferred weight ratio of the above compounds is, on the basis of isomenthone (assuming as 1), that linalool, geraniol, citral and citronellol are 0.7 to 1.5, 2.5 to 4.3, 0.6 to 1.5, and 2.0 to 3.9, respectively.

In the fragrant composition of the invention, a mixture wherein the mixture made of isomenthone, linalool, geraniol, citral and citronellol further contains a fatty acid having 8 to 10 carbon atoms may be used as an effective ingredient.

Examples of the fatty acid having 8 to 10 carbon atoms for use in the invention include octanoic acid, nonanoic acid, decanoic acid, rhodinic acid, geranic acid, and the like. The fatty acids having 8 to 10 carbon atoms may be contained solely or as a mixture of two or more of them. Of these, preferred are decanoic acid and/or rhodinic acid.

The amount of the above fatty acid present in the mixture is preferably 0.05 to 2.0 (weight ratio) on the basis of isomenthone.

The fragrant composition of the invention can be prepared by mixing the above each compound in any manner.

Since the fragrant composition itself has a mosquito-repelling effect, the fragrant composition as such may be used as a mosquito-repelling agent.

Moreover, a fragrant composition having a mosquito-repelling effect may be prepared by further adding conventional additives to the fragrant composition composed of the above mixture. In that-case, it is preferred to use 35% by weight or more of the mixture made of isomenthone, linalool, geraniol, citral and citronellol, or the mixture made of isomenthone, linalool, geraniol, citral, citronellol, and a fatty acid having 8 to 10 carbon atoms relative to the whole of the fragrant composition.

The above conventional additives include other fragrant ingredients, essential oils, plant extracts, dipropylene glycol, TEC (triethyl citrate), triglycerides, and the like. Furthermore, the fragrant composition of the invention may contain usual ingredients used for cosmetics, quasi-drugs, and medicines, for example, an antioxidant, an ultraviolet absorber, a moisturizing agent, a whitening agent, medicinal ingredients, an antiseptic, and other additives.

Moreover, for the fragrant composition of the invention, ethanol, dipropylene glycol, or the like may be used after dilution thereof.

Moreover, it is possible to increase the mosquito-repelling effect and enhance the persistency at the same time by adding a pest-repelling agent known prior to the present application, e.g., p-menthan-3, 8-diol to the fragrant composition of the invention.

The mosquitoes to be targeted by the mosquito-repelling fragrant composition of the invention are not particularly limited and examples thereof include *Culex pipiens pallen, Aedes albopictus, Anopheles gambiae, Anopheles funestus, Aedes aegypti*, and the like.

The fragrant composition of the invention may be mixed with cosmetics, quasi-drugs, and medicines commonly used for human or animals as various formulations to provide mosquito-repelling agents. For example, the composition may be mixed with lotions, aerosols, sprays, milky lotions, gels, creams, air fresheners, and the like. Moreover, the composition may be produced as solutions of alcohol, propylene glycol, benzyl benzoate, and the like, as emulsions mixed with emulsifiers, as powders adsorbed onto starch, talc, and the like, or aerosol propellants together with low-boiling hydrocarbons or low-boiling halogenated hydrocarbons.

The adding amount of the fragrant composition of the invention into final products is not particularly limited but it is preferred to add the composition into final products in the range of 1 to 10% by weight.

The following will explain the invention in further detail with reference to Examples, but the invention is not at all limited thereby. Incidentally, "%" means "% by weight" unless otherwise stated.

EXAMPLE 1

Preparation of Fragrant Composition

Based on the following formulation, a fragrant composition was prepared.

| Ingredient | % by weight |
| --- | --- |
| Isomenthone | 7.5 |
| Linalool | 7.5 |
| Geraniol | 25.0 |
| Citral | 6.5 |
| l-Citronellol | 21.0 |
| Geranic acid | 4.0 |
| Decanoic acid | 3.5 |
| Dipropylene glycol | balance |

EXAMPLE 2

Preparation of Fragrant Composition

Based on the following formulation, a fragrant composition was prepared.

| Ingredient | % by weight |
| --- | --- |
| Isomenthone | 9.0 |
| Linalool | 9.0 |
| Geraniol | 25.0 |
| Citral | 8.0 |
| l-Citronellol | 20.0 |
| Dipropylene glycol | balance |

EXAMPLE 3

Preparation of Fragrant Composition

Based on the following formulation, a fragrant composition was prepared.

| Ingredient | % by weight |
| --- | --- |
| Isomenthone | 10.0 |
| Linalool | 10.0 |
| Geraniol | 30.0 |
| Citral | 9.0 |
| l-Citronellol | 25.0 |
| Benzyl benzoate | balance |

Test Example 1
Mosquito-repelling Test 1

An ethanol solution containing 1% of the fragrant composition prepared in Example 1 was prepared and an ethanol solution containing 1% of a 1:1 mixture (weight ratio) of geraniol and l-citronellol (Comparative Example 1) was prepared.

The ethanol solution of Example 1 was applied to left hand and left foot and the solution of Comparative Example 1 was applied to right hand and right foot. Then, field test by three volunteers was conducted for 10 minutes each in the morning and in the evening in the garden where many mosquitoes inhabited and the number of mosquito bites was counted.

The results are shown in Tables 1 and 2.

TABLE 1

In the morning, 6 O'clock, temperature of 26° C.

| | Number of mosquito bites | | | |
| --- | --- | --- | --- | --- |
| | Application of 1% ethanol solution of Example 1 | | Application of Comparative Example 1 (1% ethanol solution of 1:1 mixture of geraniol and l-citronellol | |
| | Left hand | Left foot | Right hand | Right foot |
| Volunteer 1 | 0 | 0 | 6 | 5 |
| Volunteer 2 | 0 | 0 | 3 | 4 |
| Volunteer 3 | 0 | 0 | 5 | 5 |

TABLE 2

In the evening, 18 O'clock, temperature of 28° C.

| | Number of mosquito bites | | | |
| --- | --- | --- | --- | --- |
| | Application of 1% ethanol solution of Example 1 | | Application of Comparative Example 1 (1% ethanol solution of 1:1 mixture of geraniol and l-citronellol) | |
| | Left hand | Left foot | Right hand | Right foot |
| Volunteer 1 | 0 | 0 | 5 | 3 |
| Volunteer 2 | 0 | 0 | 3 | 4 |
| Volunteer 3 | 0 | 0 | 3 | 6 |

As shown in the above, the hands and foots to which an ethanol solution containing 1% of the fragrant composition obtained in Example 1 was applied were not bitten by mosquitoes though mosquitoes came near to them.

Test Example 2
Mosquito-repelling Test 2

An ethanol solution containing 1% of the fragrant composition prepared in Example 2 was prepared and an ethanol solution containing 1% of a 1:1 mixture (weight ratio) of linalool and isomenthone (Comparative Example 2) was prepared.

The ethanol solution of Example 2 was applied to left hand and left foot and the solution of Comparative Example 2 was applied to right hand and right foot. Then, field test by three volunteers was conducted for 5 minutes each in the morning and in the evening in the garden where many mosquitoes inhabited and the number of mosquito bites was counted.

The results are shown in Tables 3 and 4.

TABLE 3

In the morning, 6 O'clock, temperature of 29° C.

| | Number of mosquito bites | | | |
| --- | --- | --- | --- | --- |
| | Application of 1% ethanol solution of Example 2 | | Application of Comparative Example 2 (1% ethanol solution of 1:1 mixture of linalool and isomenthone) | |
| | Left hand | Left foot | Right hand | Right foot |
| Volunteer 1 | 1 | 0 | 5 | 2 |
| Volunteer 2 | 0 | 0 | 3 | 4 |
| Volunteer 3 | 0 | 1 | 3 | 5 |

TABLE 4

In the evening, 18 O'clock, temperature of 26° C.

| | Number of mosquito bites | | | |
| --- | --- | --- | --- | --- |
| | Application of 1% ethanol solution of Example 2 | | Application of Comparative Example 2 (1% ethanol solution of 1:1 mixture of linalool and isomenthone) | |
| | Left hand | Left foot | Right hand | Right foot |
| Volunteer 1 | 1 | 0 | 5 | 3 |
| Volunteer 2 | 0 | 0 | 4 | 4 |
| Volunteer 3 | 0 | 0 | 3 | 3 |

Reference Example 1

(Test Method)

A simple test apparatus obtainable by combining two flasks as shown in FIG. 1 was prepared. Between the two flasks, a tubular wire netting, one end of which was fixed to the flask and another end of which was removable, was provided so as to be able to circulate the air. A sugar water was set in each of Flask A and Flask B. One end of the wire netting was removed from the flask, 25 mosquitoes of *Culex pipiens pallen* were placed in the flask of the test apparatus, and the wire netting was again fixed. Then, both flasks were patted by the palm of hand to put the mosquitoes into a panic state. After it was confirmed that the number of the mosquitoes became almost the same in each flask, the number of the mosquitoes in each of both flasks was counted 1 hour after the confirmation. The same test was repeated four times.

The results are shown in Table 5.

TABLE 5

|  | Number of mosquitoes | |
| --- | --- | --- |
|  | Flask A | Flask B |
| First time | 12 | 13 |
| Second time | 13 | 12 |
| Third time | 12 | 13 |
| Fourth time | 12 | 13 |

Almost the same number of mosquitoes gathered in Flask A and Flask B and no difference was observed.

EXAMPLE 4
Preparation of Carrageenan Gel Air Freshener

A carrageenan gel air freshener was prepared based on the following formulation.

| Ingredient | % by weight |
| --- | --- |
| Carrageenan | 2.0% |
| Locust bean gum | 0.4% |
| Methylparaben | 0.1% |
| Propylene glycol | 3.0% |
| Potassium chloride | 0.3% |
| Ion-exchange water | 88.7% |
| Surfactant | 0.5% |
| Fragrant composition of Example 1 | 5.0% |

Test Example 3
Mosquito-repelling Effect in an Air Space
(Test Method)

Figure 2:
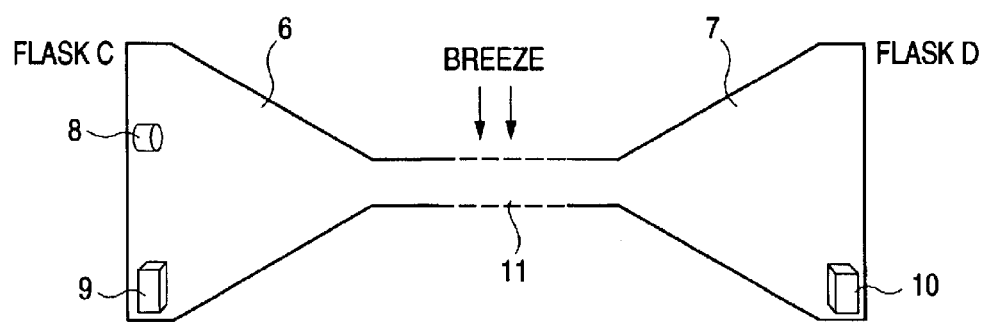
FIG. 2 is a cross-sectional view of an apparatus for measuring a mosquito-repelling effect for use in the invention.

Using a test apparatus as shown in FIG. 2, a test similar to Reference Example 1 was carried out and the number of the mosquitoes in each of both flasks was counted 1 hour after the number of the mosquitoes became almost the same in each flask. The same test was repeated four times. By the way, a sugar water and the carrageenan gel air freshener were set in Flask C, while only the sugar water was set in Flask D.

The results are shown in Table 6.

TABLE 6

|  | Number of mosquitoes | |
| --- | --- | --- |
|  | Flask C | Flask D |
| First time | 0 | 25 |
| Second time | 0 | 25 |
| Third time | 0 | 25 |
| Fourth time | 0 | 25 |

(Results)

The test was repeated four times, but, at every four-time test, the mosquitoes did not gather in Flask C in which a sugar water and the carrageenan gel air freshener were set but all mosquitoes gathered in Flask D.

In one test of the four-time tests, the test was further continued to observe the state after 65 hours. Even after 65 hours, no mosquito gathered in Flask C. In Flask D, 10 mosquitoes were alive and 15 mosquitoes were dead.

From the above results, it was apparent that the fragrant composition obtained in Example 1 exhibited a remarkably high mosquito-repelling effect.

EXAMPLE 5
Preparation of Carrageenan Gel Air Freshener

A carrageenan gel air freshener was prepared based on the following formulation.

| Ingredient | % by weight |
| --- | --- |
| Carrageenan | 2.0% |
| Locust bean gum | 0.4% |
| Methylparaben | 0.1% |
| Propylene glycol | 3.0% |
| Potassium chloride | 0.3% |
| Ion-exchange water | 91.7% |
| Surfactant | 0.5% |
| Fragrant composition of Example 2 | 2.0% |

Test Example 4
Mosquito-repelling Effect in an Air Space
(Test Method)

Using the carrageenan gel air freshener prepared in Example 5, a mosquito-repelling test was carried out once in a similar manner to Test Example 3 using 30 mosquitoes.
(Results)

The mosquitoes not at all gathered in Flask C in which the carrageenan gel air freshener prepared in Example 5 was set, while all 30 mosquitoes gathered in Flask D.

Moreover, even after 65 hours, no mosquito gathered in Flask C, and 14 mosquitoes, i.e., almost a half of the mosquitoes were dead in Flask D and remaining 16 mosquitoes were alive in Flask D.

From the above results, it was apparent that the fragrant composition prepared in Example 2 exhibited a remarkably high mosquito-repelling effect.

EXAMPLE 6
Preparation of Transparent Gel Air Freshener

Based on the following formulation, a transparent gel air freshener was prepared.

| Ingredient | % by weight |
| --- | --- |
| Gellan gum | 0.5% |
| Methylparaben | 0.1% |
| Propylene glycol | 3.0% |
| Calcium chloride, 5% aqueous solution | 0.5% |
| Ion-exchange water | 83.9% |
| Surfactant | 6.0% |
| Ethanol | 4.0% |
| Fragrant composition of Example 3 | 2.0% |

Test Example 5
Mosquito-repelling Effect in an Air Space
(Test Method)

Using the transparent gel air freshener prepared in Example 6, a mosquito-repelling test was carried out once in a similar manner to Test Example 3 using 25 mosquitoes.
(Results)

The mosquitoes not at all gathered in Flask C in which the transparent gel air freshener prepared in Example 6 was set, while all 25 mosquitoes gathered in Flask D.

Moreover, even after 65 hours, no mosquito gathered in Flask C, and 25 mosquitoes were alive in Flask D.

From the above results, it was apparent that the fragrant composition prepared in Example 3 exhibited a remarkably high mosquito-repelling effect.

Test Example 6
Blood-sucking Repelling Test

Comparative Example 3
Production Method of *Pelargonium citrosum* Extract

*Pelargonium citrosum* available at a plant shop was purchased and 5 kg of the leaves was subjected to steam distillation to obtain about 0.5 g of an essential oil. This operation was repeated three times to obtain about 1.5 g of *Pelargonium citrosum* extract.

Preparation of Test Sample Solution:

Six kinds of 1% test sample solutions were prepared by dissolving 1 g of each of the fragrant compositions of Examples 1, 2 and 3, Comparative Example 3 (*Pelargonium citrosum* extract), and Comparative Example 4 (DEET) into 90 g of ethanol and adding 9 g of water.

Test Method:

On the sample solutions of Examples 1, 2 and 3 and Comparative Examples 3 and 4, a blood-sucking repelling test toward adults of *Culex pipiens pallen* was carried out, whereby strength of mosquito-repellency and persistency were compared.

The test was carried out in a constant-temperature room kept at a temperature of 30° C. and a humidity of 70%.

After 10 ml of each test sample solution was applied onto right and left forearms, each arm was entered for 15 minutes into a bag-shape wire netting having a size of 20 cm×15 cm in which 50 each of male and female mosquitoes which were 5 to 7 days after emergence were placed, whereby the mosquitoes were allowed to suck blood. This operation was repeatedly carried out 1 hour, 2 hours, 3 hours, 4 hours, and 6 hours after the sample application, the number of sucked places within the sucking time was counted, and repellency was calculated according to the following equation. The results are shown in Table 7.

$$\text{Repellency} = [(X-Y)/X] \times 100(\%)$$

X: the number of sucked places in the case that no test sample solution was applied.

Y: the number of sucked places in the case that a test sample solution was applied.

TABLE 7

| Test sample solution | Repellency (%) | | | | |
| --- | --- | --- | --- | --- | --- |
| | After 1 hour | After 2 hours | After 3 hours | After 4 hours | After 6 hours |
| Example 1 | 100 | 100 | 100 | 100 | 100 |
| Example 2 | 100 | 100 | 100 | 100 | 100 |
| Example 3 | 100 | 100 | 100 | 100 | 100 |
| Comparative Example 3 (*Pelargonium citrosum* extract) | 100 | 95 | 88 | 66 | 34 |
| Comparative Example 4 (DEET) | 100 | 100 | 100 | 100 | 100 |

As was apparent from Table 7, the fragrant compositions obtained in Examples 1, 2 and 3 exhibited a strong repelling effect and persistency of the repellency equal to the case of DEET (Comparative Example 4). Moreover, when compared with *Pelargonium citrosum* extract (Comparative Example 3), the compositions exhibited clearly excellent mosquito-repelling effect and persistency of the repellency.

The fragrant composition of the invention exhibits a strong repelling effect almost equal to the effect of N,N-diethyl-m-toluamide (DEET) which is commonly used as a mosquito-repelling agent, and the composition exhibits no irritation toward skin and has no suspicion of carcinogenicity, so that it is a mosquito-repelling fragrant composition excellent in safety and having a pleasant smell.

Furthermore, it is also excellent in persistency of the mosquito-repelling effect and hence is of extremely high practical use.

While the invention has been described in detail and with reference to specific embodiments thereof, it will be apparent to one skilled in the art that various changes and modifications can be made therein without departing from the scope thereof.

This application is based on Japanese patent application No. 2001-336249 filed Nov. 1, 2001, the entire contents thereof being hereby incorporated by reference.

What is claimed is:

1. A fragrant composition having a mosquito-repelling effect, which comprises a mixture made of isomenthone, linalool, geraniol, citral and citronellol, as an effective ingredient, wherein the mixture further comprises a fatty acid having 8 to 10 carbon atoms.

2. The fragrant composition according to claim 1, wherein the weight ratio of isomenthone, linalool, geraniol, citral and citronellol in the mixture is, on the basis of isomenthone: linalool, geraniol, citral and citronellol are 0.5 to 2.0, 2.0 to 5.0, 0.5 to 2.0, and 2.0 to 4.0, respectively.

3. The fragrant composition according to claim 1, wherein the weight ratio of the fatty acid is 0.05 to 2.0 on the basis of isomenthone.

4. The fragrant composition according to claim 1, wherein the fatty acid having 8 to 10 carbon atoms is at least one of decanoic acid and rhodinic acid.

5. The fragrant composition according to claim 3, wherein the fatty acid having 8 to 10 carbon atoms is at least one of decanoic acid and rhodinic acid.

6. The fragrant composition according to claim 2, wherein the weight ratio of the fatty acid is 0.05 to 2.0 on the basis of isomenthone.

7. The fragrant composition according to claim 2, wherein the fatty acid having 8 to 10 carbon atoms is at least one of decanoic acid and rhodinic acid.

8. The fragrant composition according to claim 6, wherein the fatty acid having 8 to 10 carbon atoms is at least one of decanoic acid and rhodinic acid.

* * * * *

UNITED STATES PATENT AND TRADEMARK OFFICE
CERTIFICATE OF CORRECTION

PATENT NO. : 6,811,789 B2
DATED : November 2, 2004
INVENTOR(S) : Kazutoshi Sakurai, Masataka Miyasaka and Yasutaka Mishima It is certified that error appears in the above-identified patent and that said Letters Patent is hereby corrected as shown below:

Column 1,
Lines 7 and 8, delete "containing";
Line 12, delete "containing";
Line 21, delete "human" and insert -- humans --;
Line 22, after "from" insert -- the --;
Line 24, delete "rush" and insert -- rash --;
Line 41, delete "human" and insert -- humans --; before "environment" insert -- the --;
Line 44, before "human" insert -- the --.

Column 2,
Line 22, delete "containing";

Signed and Sealed this

Thirtieth Day of August, 2005

JON W. DUDAS
*Director of the United States Patent and Trademark Office*